United States Patent [19]

Miller

[11] Patent Number: 4,461,425

[45] Date of Patent: Jul. 24, 1984

[54] NEBULIZER SYSTEM

[75] Inventor: Kenneth G. Miller, Palatine, Ill.

[73] Assignee: Respiratory Care, Inc., Arlington Heights, Ill.

[21] Appl. No.: 397,841

[22] Filed: Jul. 13, 1982

[51] Int. Cl.³ .............................................. B05B 17/06
[52] U.S. Cl. .............................. 239/338; 128/203.27; 128/200.21; 239/434; 239/465; 261/DIG. 48; 261/DIG. 78
[58] Field of Search ...................... 128/200.14–200.21, 128/203.26; 239/102, 338, 19, 133, 134, 426, 434, 405; 222/146 HA, 148 H; 261/DIG. 65, 142, DIG. 48, DIG. 78

[56] References Cited

U.S. PATENT DOCUMENTS

| | | | |
|---|---|---|---|
| 3,784,104 | 1/1974 | Hartung | 239/102 |
| 3,790,086 | 2/1974 | Masai | 239/426 |
| 4,189,101 | 2/1980 | Hughes | 239/405 |
| 4,241,877 | 12/1980 | Hughes | 261/DIG. 78 |
| 4,284,590 | 8/1981 | De Boer, Jr. et al. | 239/434 |
| 4,401,241 | 8/1983 | Cruz | 128/200.21 |

Primary Examiner—Henry J. Recla
Assistant Examiner—Karin M. Reichle
Attorney, Agent, or Firm—Eric P. Schellin

[57] ABSTRACT

A portable reservoir container storing liquid, mounts on its inflow port section a heater and a vortex mixing device in series. Liquid from the bottom of the container is fed to the vortex mixing device in response to the inflow of oxygen gas thereto producing an outflow of liquid and oxygen gas in a vortical flow pattern that is delivered to the inflow port section of the container. A flow of conditioned oxygen gas is discharged from the gas space of the container through an outflow portion section.

3 Claims, 6 Drawing Figures

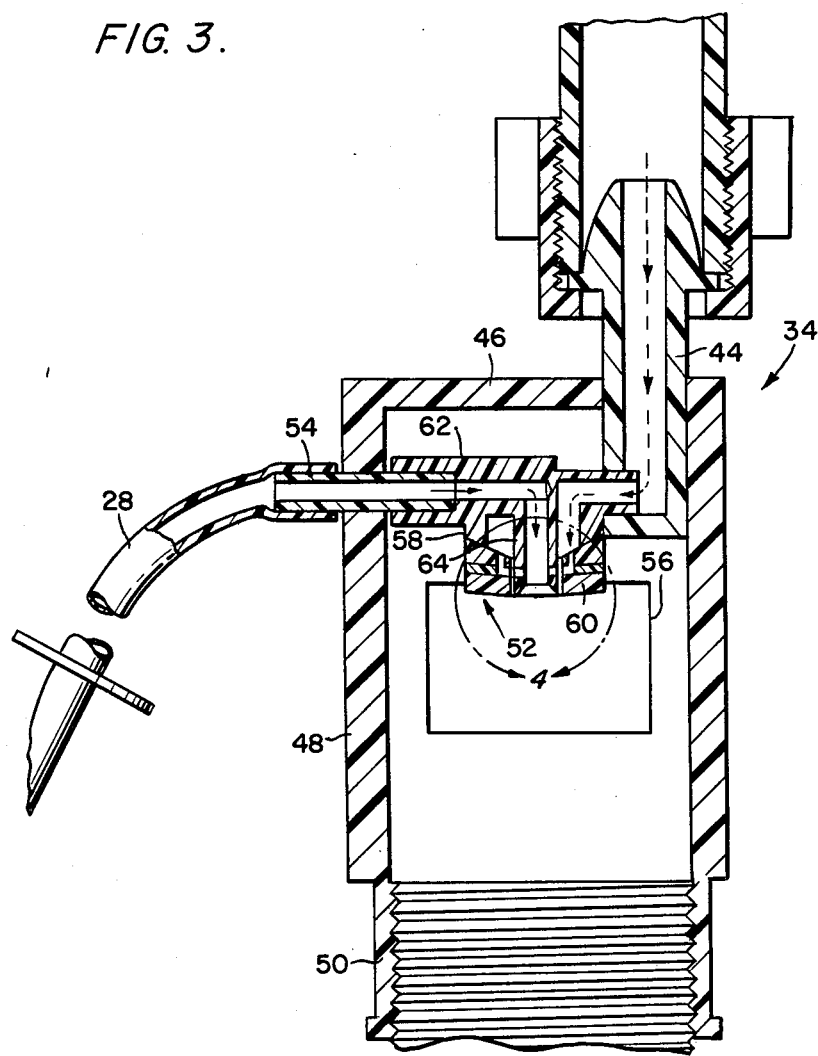
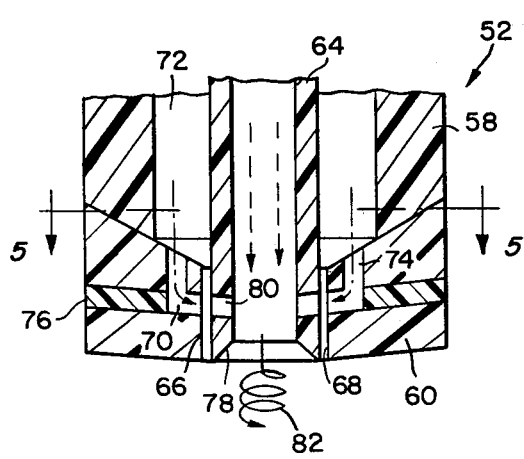
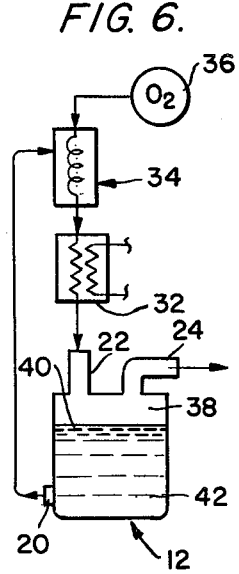
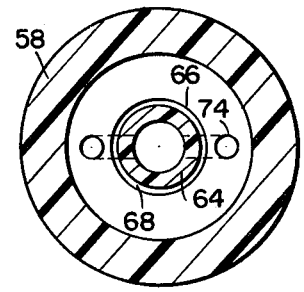

NEBULIZER SYSTEM

BACKGROUND OF THE INVENTION

Generally, nebulizing apparatus has been employed to condition oxygen being administered to a patient by mixing it with water or other liquids. In order to obtain an intimate mixture of oxygen and liquid, a vortex producing fluid flow control device has been utilized. Various installational mountings and connections have been associated with such vortex producing devices in order to feed thereto the proper quantities of oxygen and liquid and to conventiently deliver the conditioned oxygen to the patient.

Also already known in the art are portable liquid storing bottle containers suitable for use with nebulizing apparatus in supplying the desired liquid for humdifying the oxygen. One such type of bottle container is disclosed in the related copending application aforementioned.

It is therefore an important object of the present invention to provide a nebulizing system in which a portable liquid reservoir container is utilized as the source of oxygen conditioning liquid as well as to provide mounting facilities for the other components of the nebulizing system including the aforementioned vortex mixing device, the outflow or breathing tube for the patient and a heating device.

SUMMARY OF THE INVENTION

In accordance with the present invention, a portable liquid reservoir is associated with a nebulizing system, in the form of a thermoplastic bottle container within which liquid is stored at a level below inflow and outflow ports between which conditioned oxygen flows for delivery to a patient. A liquid feed port located below the level of the liquid within the container delivers liquid to a vortex type of mixing chamber device to which oxygen gas under pressure is fed from a suitable source. Misted oxygen emerges from the mixing device and is conducted through a heating device to the inflow port of the reservoir container. The mixing and heating devices are vertically interconnected in series and mounted on the tubular inflow port section associated with the container. A flexible tube is coupled to the liquid feed passage associated with the container for delivering liquid to the vortex mixing device. Thus, the flow of oxygen gas under pressure to the mixing device induces an inflow of liquid resulting in an outflow of liquid and oxygen in a vortical flow stream that is heated in the heating device before entering the liquid storing container through its inflow port section. The mixture of oxygen and liquid passes through the gas space at the upper end of the liquid storing container and is discharged through the outflow port section to the patient.

BRIEF DESCRIPTION OF DRAWING FIGURES

The foregoing invention is hereinafter described in greater detail with reference to the accompanying drawings, wherein:

FIG. 3 is an enlarged partial side section view through the vortex mixing component associated with the apparatus shown in FIGS. 1 and 2.

FIG. 4 is an enlarged partial section view of a portion of the device denoted by 4 in FIG. 3.

FIG. 5 is a transverse section view taken substantially through a plane indicated by section line 5—5 in FIG. 4.

FIG. 6 is a schematic circuit diagram representing the system associated with the present invention.

DETAILED DESCRIPTION OF PREFERRED EMBODIMENT

Figure 1:
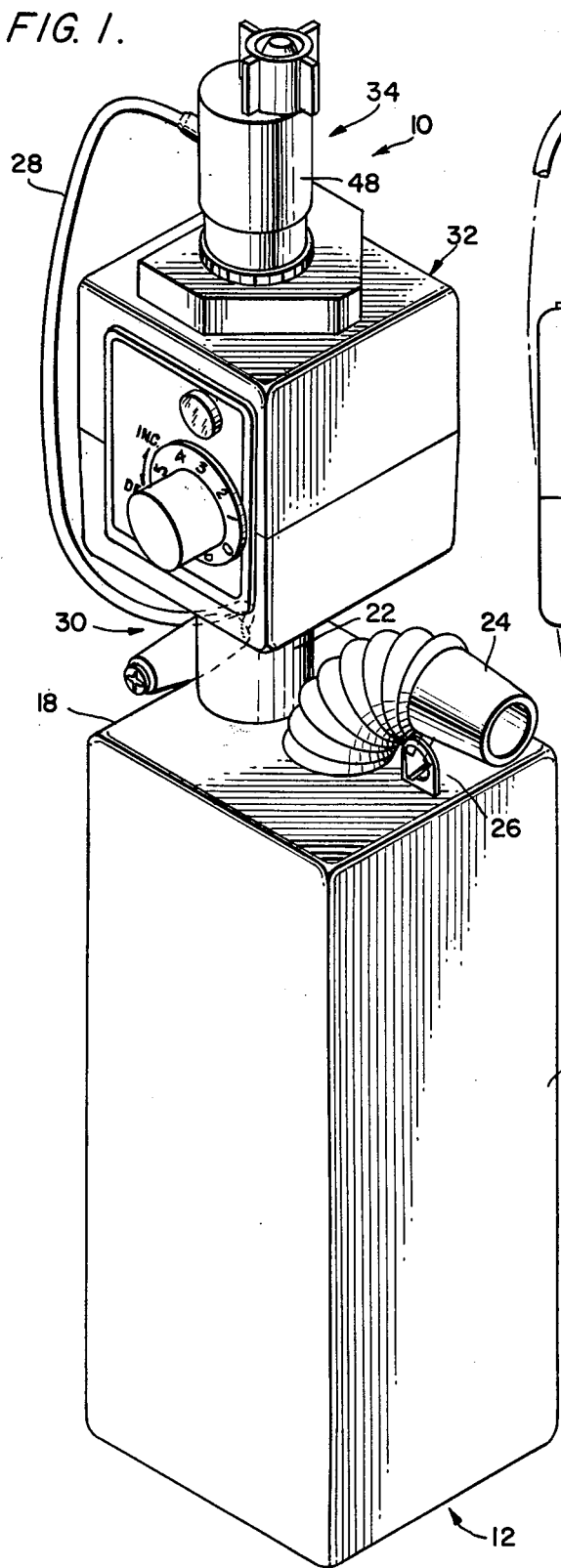
FIG. 1 is a perspective view illustrating a nebulizing apparatus constructed in accordance with the present invention.
Figure 2:
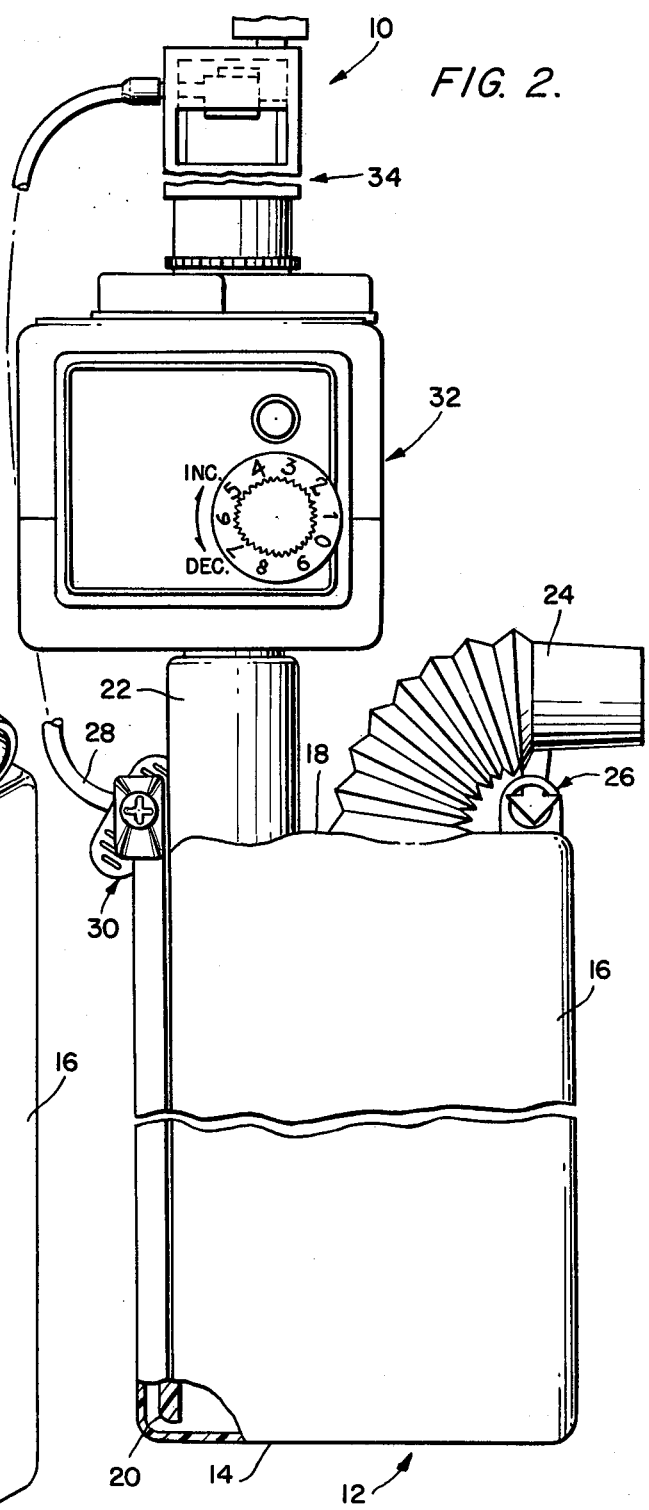
FIG. 2 is a partial side elevation view of the apparatus shown in FIG. 1.

Referring now to the drawings in detail, FIGS. 1 and 2 illustrate a nebulizing apparatus generally referred to by reference numeral 10. The apparatus includes a portable liquid storing reservoir bottle container 12 as disclosed in the copending application aforementioned. The reservoir container is blow-molded from a thermoplastic material and includes a bottom wall 14 interconnected with vertical side walls 16 and a top end wall 18 to enclose a liquid storing chamber therein. A liquid feed port is established by a tubular passage formation 20 through which liquid is drawn from the bottom of the container. Fluid is introduced into the top of the container through a tubular inflow port section 22 while conditioned oxygen is discharged from the top of the container to the patient through an outflow port section 24 that is bent to an operative position as shown and releaseably held in such position by means of latch means 26 as described in detail in the aforementioned copending application. The liquid from the container is delivered to a location externally thereof through a flexible tube 28 that is coupled by means of a coupling assembly 30 to the upper end of the liquid feed port formation 20 as also described in detail in the aforementioned copending application.

Mounted on the inflow port section 22 is a heating device 32 of any suitable type already known in the art. A flow stream of oxygen mixed with liquid is conducted through the heating device to the inflow port section 22 and is heated to a desired temperature within the heating device. Mixing of oxygen with liquid is accomplished within a vortex type of mixing chamber device generally referred to by reference numeral 34 physically mounted on top of the heating device as shown. Liquid is supplied to the mixing device 34 through the flexible tube 28 while oxygen gas under pressure is supplied thereto from a suitable pressurized source 36 as diagrammatically shown in FIG. 6.

As more clearly seen in FIG. 6, pressurized oxygen gas is mixed with the liquid delivered thereto from the bottom of container 12 and emerges in a vortical flow stream that passes through the heater 32 within which the oxygen and liquid mixture is heated. The heated mixture of oxygen and liquid enter an upper gas space 28 within the container 12 above the level 40 of the liquid 42 stored therein. The mixture of liquid and oxygen gas passing through the gas space is discharged through the outflow section 24 for patient inhalation purposes. The inflow and outflow port sections 22 and 24 are therefore located above the liquid level 40 while the liquid feed port 20 is located below the liquid level 40 for proper operation of the nebulizing system.

As shown in FIGS. 3, 4 and 5, oxygen gas under pressure enters the vortex device 34 through an inflow tube 44 that projects through the top wall 46 of an outer cylindrical housing 48, having a lower internally threaded portion 50 through which the vortex mixing device is threadedly connected to the heating device 32 therebelow. The inflow tube 44 is connected to a flow control assembly 52 supported between the inflow tube 44 and a liquid infeed tube 54 connected to the upper end of housing 48. The flexible tube 28 is coupled to the liquid infeed tube 54 as shown. Flow of oxygen gas under pressure through the flow control assembly 52 induces an inflow of liquid through liquid infeed tube 54 to produce a discharge of oxygen gas and liquid from the lower end of the flow control assembly 52. Thus, the liquid and oxygen expands into the enclosure of housing 48 to develop a vortical flow stream that proceeds downwardly into the heating device. An adjusted inflow of ambient air may enter the housing 48 through the openings 56 formed therein.

As more clearly seen in FIGS. 4 and 5, the flow control assembly 52 includes a cylindrical housing 58 having a flow restricting wall 60 secured thereto at a lower axial end opposite an upper axial end to which an upper closing wall 62 is connected as shown in FIG. 3. The liquid infeed tube 54 introduces liquid into the tubular conduit 64 of the housing 58 adjacent the upper wall 62 while the inflow of oxygen gas under pressure enters the upper axial end of the chamber. A tubular conduit 64 extends concentrically through the housing 58 and a central opening 66 formed in the lower end wall 60 with radial clearance so as to form an annular space 68. The lower wall 60 is formed with radially extending, restricted flow passages 70 that are in fluid communication with the chamber 72 through connecting bores 74. Plugs 76 close those portions of the radially extending passages 70 beyond their intersections with the bores 74. Accordingly, restricted, right angular flow of oxygen gas from the chamber 72 enters the liquid flow stream in the conduit 64 adjacent the lower discharge end 78, through openings 80 aligned with the radially extending passages 70. The foregoing restricted flow passage arrangement results in the discharge of liquid and oxygen gas in a vortical flow pattern denoted by reference numeral 82 in FIG. 4, as the discharging liquid and oxygen expands into the enclosure of housing 48.

It has been found that when a vortex mixing device of the foregoing type is associated with the nebulizing system as hereinbefore described, a particularly desirable oxygen gas mixture is delivered to the patient for inhalation therapy purposes.

What is claimed is:

1. In combination with a liquid storing container having an inflow port, an outflow port and a liquid feed port, a nebulizer system including a source of oxygen gas under pressure, vortex mixing means connected to said source and said liquid feed port for mixing the oxygen gas and the liquid to produce a vortical flow stream of a mixture of the liquid and the oxygen, means interconnected between the vortex mixing means and the inflow port of the container for conducting said vortical flow stream into the container through said inflow port producing an outflow of conditioned oxygen from the outflow port, and heating means mounted on the container in heat exchange relation to the conducting means for heating the mixture in the vortical flow stream, said heating means and the vortex mixing means being connected in series between the source and the inflow port, wherein said vortex mixing means includes a housing having upper and lower axial ends enclosing a receiving chamber therebetween, an end wall connected to the housing closing said upper axial end, means connected to the source for introducing the oxygen gas to the receiving chamber adjacent said upper end wall, conduit means connected to the liquid feed port and extending through the receiving chamber from said upper end wall for discharge of the liquid from said lower axial end of the receiving chamber, flow restricting wall means connected to said housing at said lower axial end in radially spaced relation to the conduit means for directing restricted discharge of the oxygen gas into the liquid being discharged while the liquid is inside said conduit means, and an annular space extending from said chamber through said lower axial end to produce said vortical stream flow.

2. In combination with a liquid storing container having an inflow port, an outflow port and a liquid feed port, a nebulizer system including a source of oxygen gas under pressure, vortex mixing means connected to said source and said liquid feed port for mixing the oxygen gas and the liquid to produce a vortical flow stream of a mixture of the liquid and the oxygen, means interconnected between the vortex mixing means and the inflow port of the container for conducting said vortical flow stream into the container through said inflow port producing an outflow of conditioned oxygen from the outflow port, and heating means mounted on the container in heat exchange relation to the conducting means for heating the mixture in the vortical flow stream, wherein said vortex mixing means includes a housing having upper and lower axial ends enclosing a receiving chamber therebetween, an end wall connected to the housing closing said upper axial end, means connected to the source for introducing the oxygen gas to the receiving chamber adjacent said upper end wall, conduit means connected to the liquid feed port and extending through the receiving chamber from said upper end wall for discharge of the liquid from said lower axial end of the receiving chamber and flow restricting wall means connected to the housing at said lower axial end in radially spaced relation to the conduit means for directing restricted discharge of the oxygen gas into the liquid while the liquid is inside said conduit means, and an annular space extending from said chamber through said lower axial end.

3. In combination with a liquid storing container having an inflow port, an outflow port and a liquid feed port, a nebulizer system including a source of oxygen gas under pressure, vortex mixing means connected to said source and the liquid feed port for mixing the oxygen gas and the liquid, and means interconnected between the vortex mixing means and the inflow port of the container for conducting a flow stream of the liquid and the oxygen gas into the container through said inflow port producing an outflow of conditioned oxygen from the outflow port, said vortex mixing means including a conduit having an outlet end from which the liquid is discharged into said flow stream, flow restricting means mounted in radially spaced relation to the conduit at said outlet end thereof for directing a restricted flow of the oxygen gas into the liquid while the liquid is inside said conduit, and an annular space extending beyond the outlet end of said conduit to induce vortical flow of said flow stream.

* * * * *